United States Patent
Eckhardt

[11] Patent Number: 6,106,041
[45] Date of Patent: Aug. 22, 2000

[54] DEVICE FOR REMOVING TICKS

[75] Inventor: Friedhelm Eckhardt, Siegen, Germany

[73] Assignee: ECKHARDT Abform- und Giesstechnik GmbH, Mudersbach, Germany

[21] Appl. No.: 09/335,137

[22] Filed: Jun. 17, 1999

[30] Foreign Application Priority Data

Jun. 22, 1998 [DE] Germany .......................... 198 27 651

[51] Int. Cl.⁷ ............................... A01M 3/00; B25B 9/02
[52] U.S. Cl. ........................................ 294/99.2; 606/210
[58] Field of Search ............................. 294/8.5, 33, 99.1, 294/99.2, 100, 115, 116; 606/206, 210

[56] References Cited

U.S. PATENT DOCUMENTS

| | | | |
|---|---|---|---|
| 3,420,563 | 1/1969 | Witt | 294/100 X |
| 5,002,323 | 3/1991 | Idsund | 294/100 |
| 5,078,729 | 1/1992 | Eichhorn | 294/99.2 X |
| 5,407,243 | 4/1995 | Riemann | 294/100 |

FOREIGN PATENT DOCUMENTS

| | | |
|---|---|---|
| 0717963 | 6/1996 | European Pat. Off. . |
| 8015364 | 10/1980 | Germany . |
| 196 52 218 A1 | 6/1998 | Germany . |

*Primary Examiner*—Johnny D. Cherry
*Attorney, Agent, or Firm*—Friedrich Kueffner

[57] ABSTRACT

A device for removing ticks includes two partially elastic gripping arms, wherein gripping jaws provided at the free ends of the gripping arms are pressed together with a defined closing force. The gripping jaws can be opened for receiving a tick by pressing against handle pieces integrally formed on the gripping arms. The gripping arms are integrally connected to each other through an elastic support web at a location between the gripping jaws and the handle pieces. With their inner ends facing away from the gripping jaws, the gripping arms rest against inclined surfaces which are integrally formed in the interior of a housing which receives the gripping arms. In the assembled state of the device, the defined closing force is produced by the contact of the inner gripping arm ends at the inclined surfaces together with the internal elasticity of the gripping arms.

7 Claims, 2 Drawing Sheets

DEVICE FOR REMOVING TICKS

BACKGROUND OF THE INVENTION

1. Field of the Invention

The present invention relates to a device for removing ticks which includes two partially elastic gripping arms, wherein gripping jaws provided at the free ends of the gripping arms are pressed together with a defined closing force. The gripping jaws can be opened for receiving a tick by pressing against handle pieces integrally formed on the gripping arms.

2. Description of the Related Art

A device of the above-described type in the form of a cross-forceps is disclosed in EP 0 717 963 Al. In this known device, the gripping arms cross each other or intersect each other in such a way that the gripping jaws rest against each other under a pretensioning force and the mouth formed in this manner can be opened by overcoming the pretensioning force.

Similar cross-forceps for removing ticks are described in DE-GM 80 15 364 and DE 196 52 218 Al.

The manufacture and assembly of these known devices for removing ticks are relatively expensive and complicated.

SUMMARY OF THE INVENTION

Therefore, it is the primary object of the present invention to provide a device for the removal of ticks which is composed of only two injection molded parts of synthetic material which can be easily and quickly assembled.

In accordance with the present invention, the gripping arms are integrally connected to each other through an elastic support web at a location between the gripping jaws and the handle pieces. With their inner ends facing away from the gripping jaws, the gripping arms rest against inclined surfaces which are integrally formed in the interior of a housing which receives the gripping arms. In the assembled state of the device, the defined closing force is produced by the contact of the inner gripping arm ends at the inclined surfaces together with the internal elasticity of the gripping arms.

The device according to the present invention composed of only two injection molded parts of synthetic material can be easily and quickly assembled by inserting the gripping arms merely into the housing, wherein the handle pieces which are used for opening the gripping jaws for placing them against a tick on the skin, engage in recesses of the housing. The gripping jaws at the front ends of the gripping arms then protrude out of a front opening of the housing and rest against each other with a predetermined closing force which is produced by the internal elasticity of the gripping arms which are integrally injection molded of elastic synthetic material and whose inner ends rest in the assembled state of the device against inclined surfaces in the housing and pretension the gripping arms as a result.

The various features of novelty which characterize the invention are pointed out with particularity in the claims annexed to and forming a part of the disclosure. For a better understanding of the invention, its operating advantages, specific objects attained by its use, reference should be had to the following descriptive matter in which there are described preferred embodiments of the invention.

DESCRIPTION OF THE PREFERRED EMBODIMENTS

Figure 1:
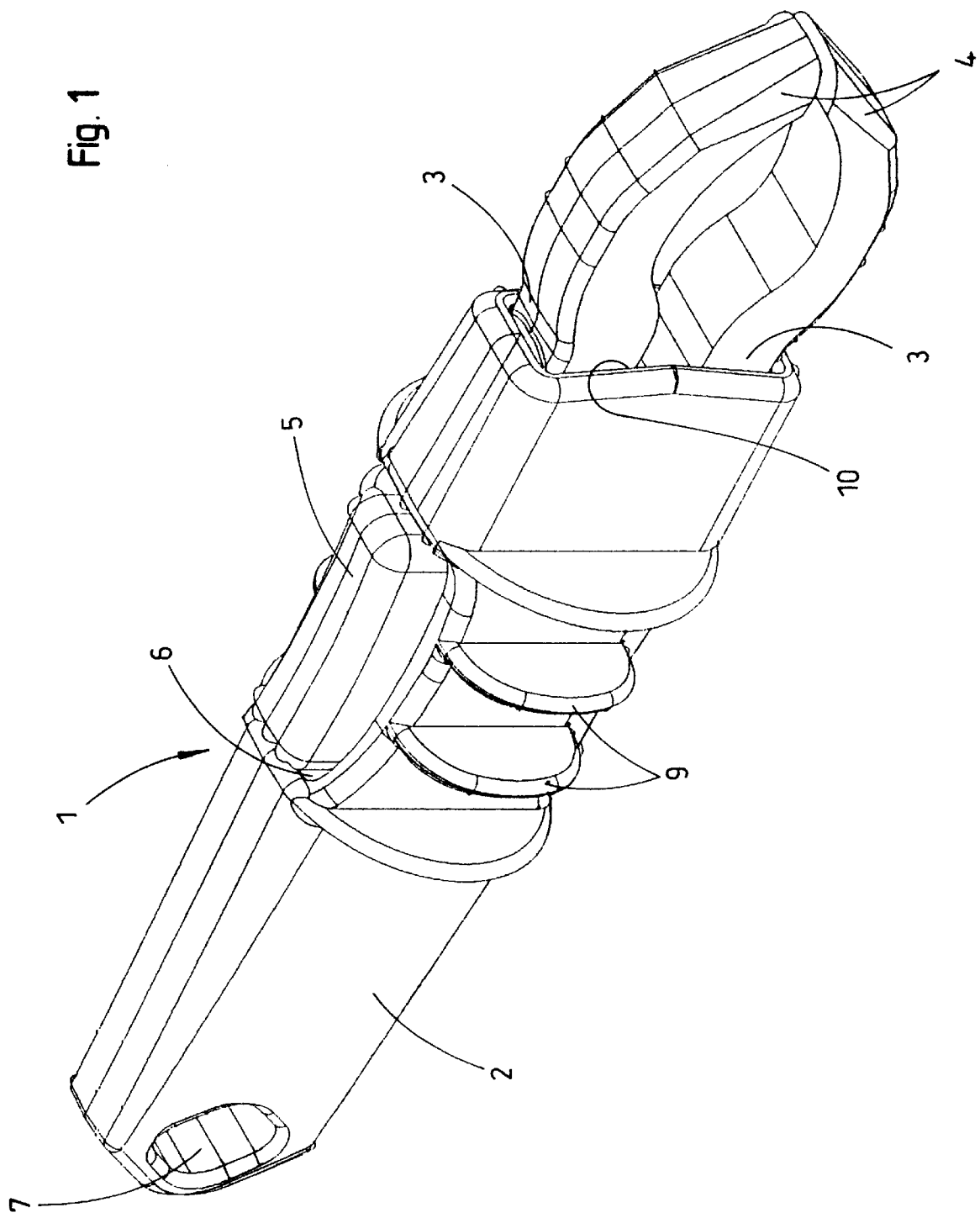
FIG. 1 is a perspective view of an embodiment of the device for removing ticks according to the present invention.

The device 1 for removing ticks illustrated in FIG. 1 of the drawing is composed of only two parts, each integrally injection molded of synthetic material. The two parts are a housing 2 which is advantageously injection molded in one piece of an inelastic synthetic material, and the second part is the gripping arms 3 integrally injection molded of elastic synthetic material. Gripping jaws 4 are integrally formed at the front or outer ends of the gripping arms 3. The gripping jaws 4 protrude out of the housing 2. Grip or handle pieces 5 of the gripping arms 3 engage in corresponding openings 6 of the housing 2.

Figure 2:
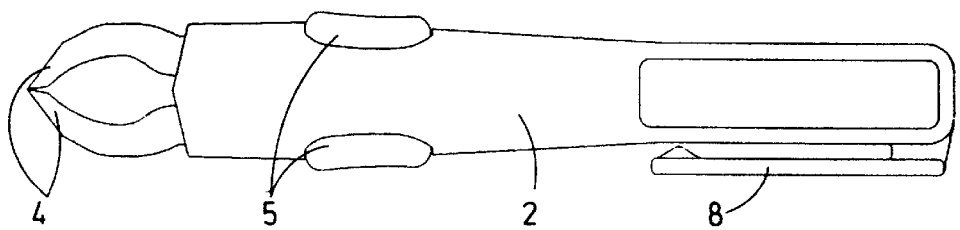
FIG. 2 is a side view of another embodiment of the device.
Figure 3:
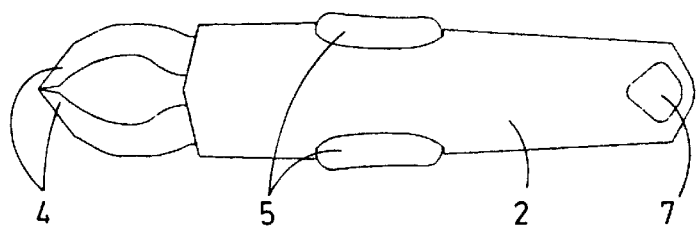
FIG. 3 is a side view of the embodiment of FIG. 1.

In the embodiment illustrated in FIGS. 1 and 3 to 6, the housing 2 has an eyelet 7 for hanging up the device. In the embodiment illustrated schematically in FIG. 2, the device 1 has a holding clip 8 integrally formed on the housing 2, so that the device 1 can be carried in a pocket of an article of clothing in the same manner as, for example, a ball point pen.

As can be seen in FIG. 1, the housing 2 has on the level of the handle pieces 5 laterally protruding round ribs 9, so that the device 1 can be easily turned if necessary after gripping a tick.

Figure 4:
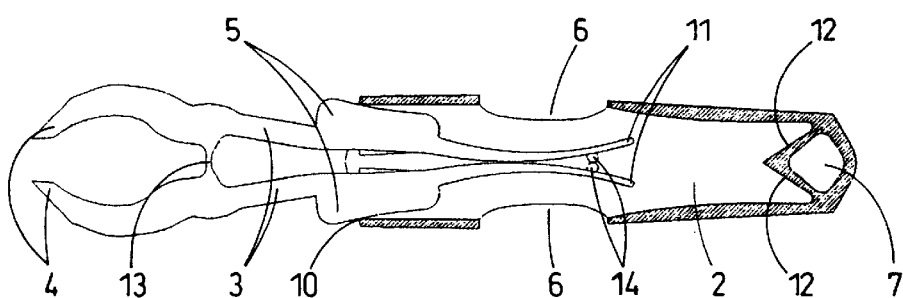
FIG. 4 is an illustration of the initial phase of the assembly of the two injection molded parts of the device.
Figure 5:
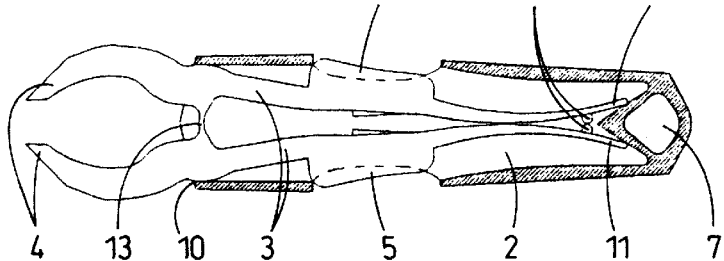
FIG. 5 is an illustration of the device shown in the opened state.
Figure 6:
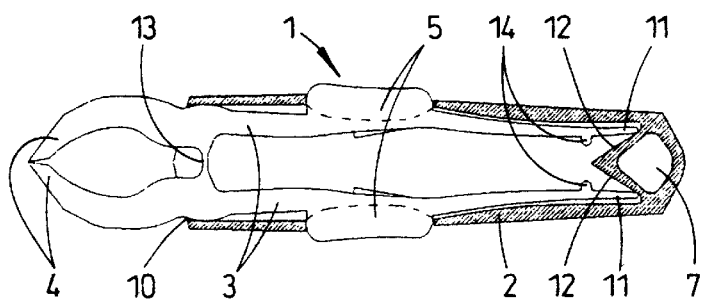
FIG. 6 is an illustration of the device shown in the closed state.

The initial phase of the assembly of the two parts 2 and 3 of the device 1 is illustrated in FIG. 4. The housing 2 is open at its front end and the gripping arms 3 are pushed in the pressed-together state into this opening 10 of the housing 2, as seen in FIG. 4, until the rearward or inner ends 11 of the gripping arms 3 make contact with inclined surfaces 12 in the housing 2, as shown in FIG. 5. After the gripping arms 3 have been completely inserted into the housing 2, as shown in FIG. 6, the handle pieces 5 engage in the openings 6 of the housing 2.

The gripping arms 3 are connected to each other through a support web 13 which serves as an elastic pivot bearing between the gripping arms 3. In order to ensure that the inner ends 11 of the gripping arms 3 can securely slide onto the inclined surfaces 12 when the gripping arms 3 are inserted into the housing 2, support projections 14 are provided at a certain distance from the inner or rearward ends 11, wherein the support projections 14, as can be seen in FIGS. 4 and 5, serve to spread apart the inner or rearward ends 11 when the gripping arms 3 are pressed together. When the gripping arms 3 are completely inserted, the inner ends 11 of the gripping arms 3 are supported by the inclined surfaces 12 and bent up in such a way that the gripping jaws 4 are pressed together, so that the supporting web 13 is subjected to slight tensile stress.

For using the device 1, the handle pieces 5 within the openings 6 of the housing 2 are pressed in, so that the gripping jaws 4 open. The opening width of the gripping jaws 4 can be selected as required and does not have to be as large as illustrated in FIG. 4 in which only the initial phase of the assembly is shown.

Figure 7:
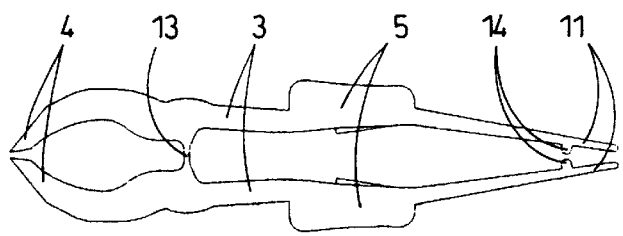
FIG. 7 is a separate illustration of the gripping arms.

FIG. 7 of the drawing shows, separately in a side view, the gripping arms 3 manufactured integrally as one piece.

When the handle pieces 5 are pressed together, i.e., when the device 1 is opened as shown in FIG. 5, it can be seen that the inner ends 11 of the gripping arms 3 slide downwardly on the inclined surfaces 12 as a result of being shortened due to being bent. This significantly reduces the pretension in the resilient gripping arms 3 and prevents an overextension of the gripping arms 3.

While specific embodiments of the invention have been described in detail to illustrate the inventive principles, it will be understood that the invention may be embodied otherwise without departing from such principles.

I claim:

1. A device for removing ticks comprising two partially elastic gripping arms having free ends, gripping jaws provided at the free ends and pressed together with a defined closing force, the gripping arms having handle pieces integrally formed on the gripping arms, wherein the gripping jaws can be opened by pressing the gripping pieces for receiving a tick, wherein the gripping arms are integrally connected to each other through an elastic support web at a location between the handle pieces and the gripping jaws, the device further comprising a housing integrally formed of a single piece for receiving the gripping arms, the gripping arms having inner ends facing away from the gripping jaws, wherein the housing has in an interior thereof integrally formed inclined surfaces, wherein the inner ends of the gripping arms rest against the inclined surfaces, such that, in an assembled state of the device, the contact of the inner ends of the gripping arms with the inclined surfaces and an internal elasticity of the gripping arms produce the defined closing force.

2. The device according to claim 1, wherein the gripping arms have integrally formed support projections facing each other and located at a distance from the inner ends from the gripping arms, wherein, when the gripping arms are inserted into the housing, the inner ends of the gripping arms are spread apart and can slide onto the inclined surfaces.

3. The device according to claim 1, wherein the housing has openings, and wherein, when the gripping arms are completely inserted into the housing, the handle pieces engage in the openings.

4. The device according to claim 1, wherein the gripping arms are injection molded as a single piece of an elastic synthetic material and the housing is injection molded as a single piece of an inelastic synthetic material.

5. The device according to claim 1, further comprising a holding clip integrally formed on the housing.

6. The device according to claim 1, further comprising an eyelet integrally formed on the housing.

7. The device according to claim 1, wherein the housing has laterally protruding round ribs located adjacent the handle pieces.

* * * * *